United States Patent [19]
Mills et al.

[11] Patent Number: 5,289,824
[45] Date of Patent: Mar. 1, 1994

[54] WRIST-WORN ECG MONITOR

[75] Inventors: Gary N. Mills, Gladstone; Habib Homayoun, Aloha, both of Oreg.

[73] Assignee: Instromedix, Inc., Hillsboro, Oreg.

[21] Appl. No.: 816,389

[22] Filed: Dec. 26, 1991

[51] Int. Cl.$^5$ .............................................. A61B 5/02
[52] U.S. Cl. ................................... 128/696; 128/702; 128/904
[58] Field of Search .............. 128/696, 700, 702, 672, 128/690, 903, 904

[56] References Cited

U.S. PATENT DOCUMENTS

| | | | |
|---|---|---|---|
| 3,972,320 | 8/1976 | Kalman | 128/690 |
| 4,108,166 | 8/1978 | Schmid | 128/690 |
| 4,129,125 | 12/1978 | Lester et al. | 128/702 X |
| 4,256,117 | 3/1981 | Perica et al. | 128/690 |
| 4,409,983 | 10/1983 | Albert | 128/690 |
| 4,425,921 | 1/1984 | Fujisaki et al. | 128/690 |
| 4,603,704 | 8/1986 | Mund et al. | 128/784 |
| 4,799,491 | 1/1989 | Eckerle | 128/672 |
| 4,802,488 | 2/1989 | Eckerle | 128/672 |
| 4,928,690 | 5/1990 | Heilman et al. | 128/421 |
| 4,938,228 | 7/1990 | Righter et al. | 128/690 |
| 5,154,183 | 10/1992 | Kreyenhagen et al. | 128/785 |
| 5,191,891 | 3/1993 | Righter | 128/710 |

FOREIGN PATENT DOCUMENTS

| | | | |
|---|---|---|---|
| 2753165 | 11/1978 | Fed. Rep. of Germany | 128/690 |
| 2845679 | 4/1980 | Fed. Rep. of Germany | 128/690 |
| 8119650 | 10/1981 | France | |

OTHER PUBLICATIONS

"Inventors of Heart Monitor Tick Toward Prosperity . . ." (Oregon business Journal), Brock, Sep. 17, 1990.

Primary Examiner—Lee S. Cohen
Assistant Examiner—Jeffrey R. Jastrzab
Attorney, Agent, or Firm—Kolisch, Hartwell, Dickinson, McCormack & Heuser

[57] ABSTRACT

A compact, lightweight wrist-worn cardiac data and event monitor having dry skin electrodes integral with the monitor's housing is disclosed. Preferably, the skin electrodes are made of titanium nitride-plated stainless steel and form inner, wrist-contacting, and outer, other hand's palm-contactable regions of the housing. Chronometric and other multiple functions are provided to increase the functional density of the monitor by partitioning and very-large-scale-integrating the circuitry, which includes signal detection; data conversion, storage, display and telecommunication; and external push-button controls operable by the patient's other hand. In accordance with the preferred embodiment, a telephonic transmitter is integrally included within the housing for remote diagnostic purposes without the need for external connections. By a preferred method of the invention, a simplified digital filter implemented in firmware ensures that only ECG and event data are recorded at the exclusion of noise and motion artifacts. By another preferred method of the invention, a battery life prediction method is used to extend the useful life of the battery and to indicate to the patient when the battery should be replaced. Event data that may be recorded and tele-transmitted along with the ECG data include time-of-day or elapsed time markers, as well as markers or indications of the detection of any pulses produced, for example, by an implanted pacemaker or an implanted cardio-verter/defibrillator monitor (ICDM).

10 Claims, 6 Drawing Sheets

WRIST-WORN ECG MONITOR

BACKGROUND AND SUMMARY OF THE INVENTION

The invention generally relates to wrist-worn cardiac monitors. More particularly, the invention concerns a wrist-worn ECG monitor having integral electrodes for recording and teletransmitting ECG data to a remote site for analysis by a diagnostician.

Known wrist-worn cardiac monitors are extremely limited in functionality. For example, some conventional monitors simply monitor and display pulse rate and thus provide no ECG data recording capability at all. Others record ECG data and provide only for the local playback of recorded data and thus provide no remote diagnostic capability. Still others require external electrodes on the ends of a cable for detection of an ECG signal near the heart of the cardiac patient—often necessitating the use of messy conductive gels—and thus are difficult to hook up and use, especially for long-term monitoring of a relatively active patient. Problems abound in producing small, lightweight ECG monitors that provide for long-term cardiac event recording and remote professional diagnostic and prescriptive patient care.

Accordingly, it is a principal object of the present invention to provide a self-contained, wrist-worn ECG monitor that provides at least single event recording and telecommunication of ECG data to a remote site for professional diagnosis.

It is another important object of the invention to provide such a monitor with the greatest possible functionality in an extremely compact, integral housing.

Yet another object is to provide such a monitor that reliably detects and records ECG signals without the use of external electrodes or messy gels or other skin preparation.

It is also an object of the invention to provide an improved dry skin electrode system that is an integral part of the housing of such a monitor.

Another object is to render such a wrist-worn monitor that easily and conveniently can be used by a cardiac patient without assistance by another, for long-term ambulatory patient care.

Still another object is to make such a wrist-worn ECG monitor the multiple functions of which readily can be operated with the patient's other hand.

One equally important object is to provide such functionality in a lightweight, compact, wrist-worn monitor that yet has the capacity to record multiple events that may occur over a long period of time, e.g. days.

One other object of the invention is to make such a monitor easily manufactured and maintained, and cost effective.

Briefly summarizing the invention in its preferred embodiment, a wrist-worn monitor is provided that, without external connections of any kind, enables local, multiple event ECG data recording and telecommunication to a remote site, as well as providing the time and date functions normally provided by a wristwatch. The monitor is housed in an extremely compact and lightweight housing and is operable by the patient's simply placing the other palm over a portion of the monitor's face to contact an upper skin electrode. Custom very-large-scale integrated (VLSI) circuit components contained within the housing include ECG signal and abnormal event detection circuitry, analog-to-digital (AD) and digital-to-analog (DA) conversion circuitry, memory and processor circuitry for scanning the pushbuttons and displaying selected chronometric, cardiac and status information. Circuitry is also provided to drive an integral speaker for the telecommunication of ECG signal or cardiac event data via telephone lines to a remote site for so-called "over-read", diagnosis and archival recording.

The monitor's housing includes dual, integral dry skin electrodes located on a wrist-contacting, inner or rear base plate and on an outer or front surface contactable by the palm of the patient's other hand. The electrodes preferably are formed by plating a region of a stainless steel or other base metal expanse with a thin layer of titanium nitride (TiN), titanium carbide (TiC) or titanium carbo-nitride (TiCN). The microprocessor and associated electronics, including firmware executed thereby, employs a digital bandpass filter reliably to detect ECG signals characterized by QRS complexes or pacer and defibrillator pulses but to ignore noise and motion artifacts. A current draw measuring method implemented by the microprocessor and associated electronics monitors usage and predicts the end of life of the integral battery beyond which monitoring is halted, thereby to maximize long-term monitoring capacity, to avoid potentially inaccurate ECG data recording and to inform the patient when the battery should be replaced.

These and other objects and advantages of the invention will be more clearly understood from a consideration of the accompanying drawings and the following description of the preferred embodiment.

DETAILED DESCRIPTION OF THE PREFERRED EMBODIMENT

Figure 1:
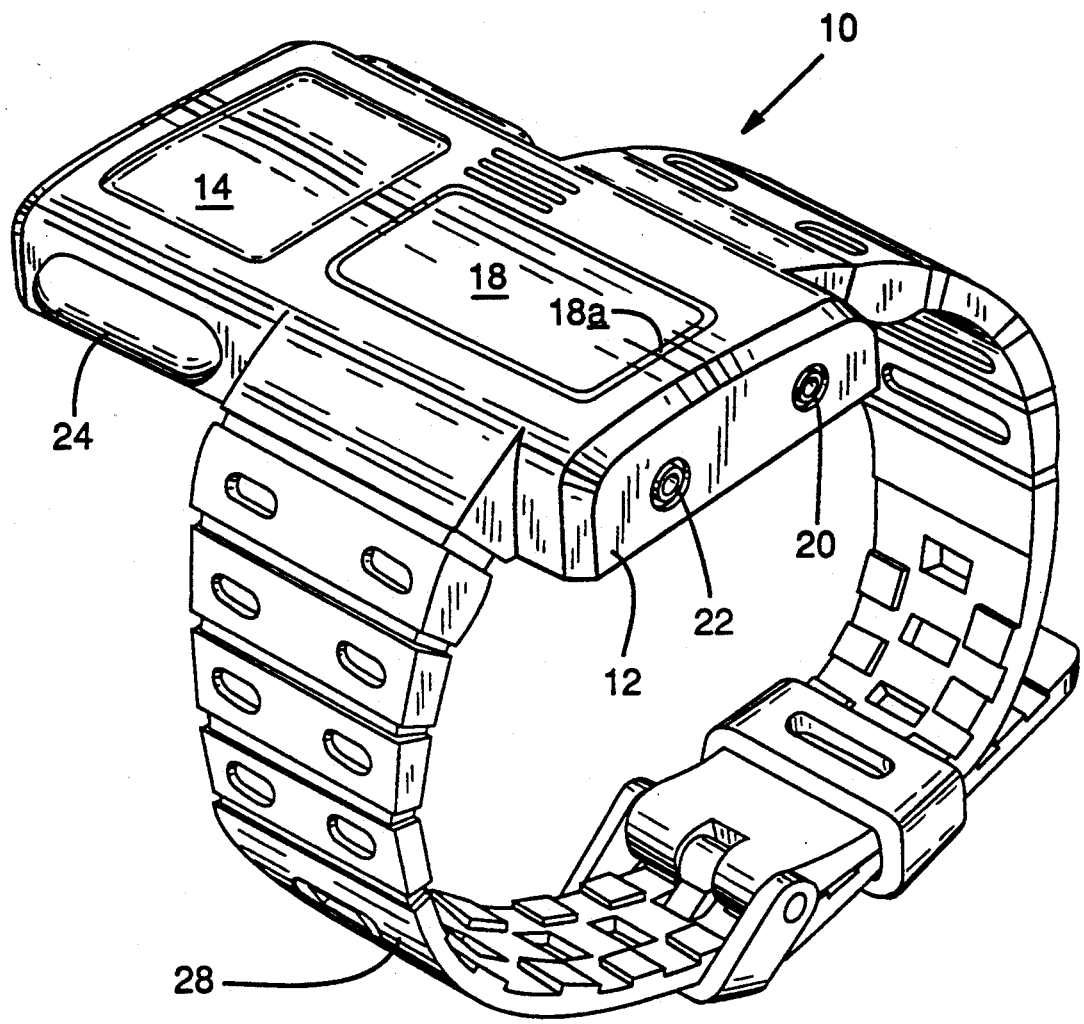
FIG. 1 is an isometric view of the wrist-worn ECG monitor made in accordance with the preferred embodiment of the invention.

Referring first and briefly to FIG. 1, the apparatus of the invention made in accordance with its preferred embodiment is indicated in isometric view at 10. It may be seen from FIG. 1 that apparatus 10, which is drawn generally in enlarged but otherwise accurate scale, is am extremely compact and lightweight, extremely full function cardiac monitor that conveniently and comfortably can be wrist-worn by a cardiac patient, because the form factor and size of the monitor's housing relative to the conventional wrist band is only slightly larger than a traditional digital watch. The full functionality of apparatus 10, which provides unprecedented functional density and convenience due to its fully integrated dry skin electrodes, will be described in detail by reference to FIGS. 2-6.

Figure 2:
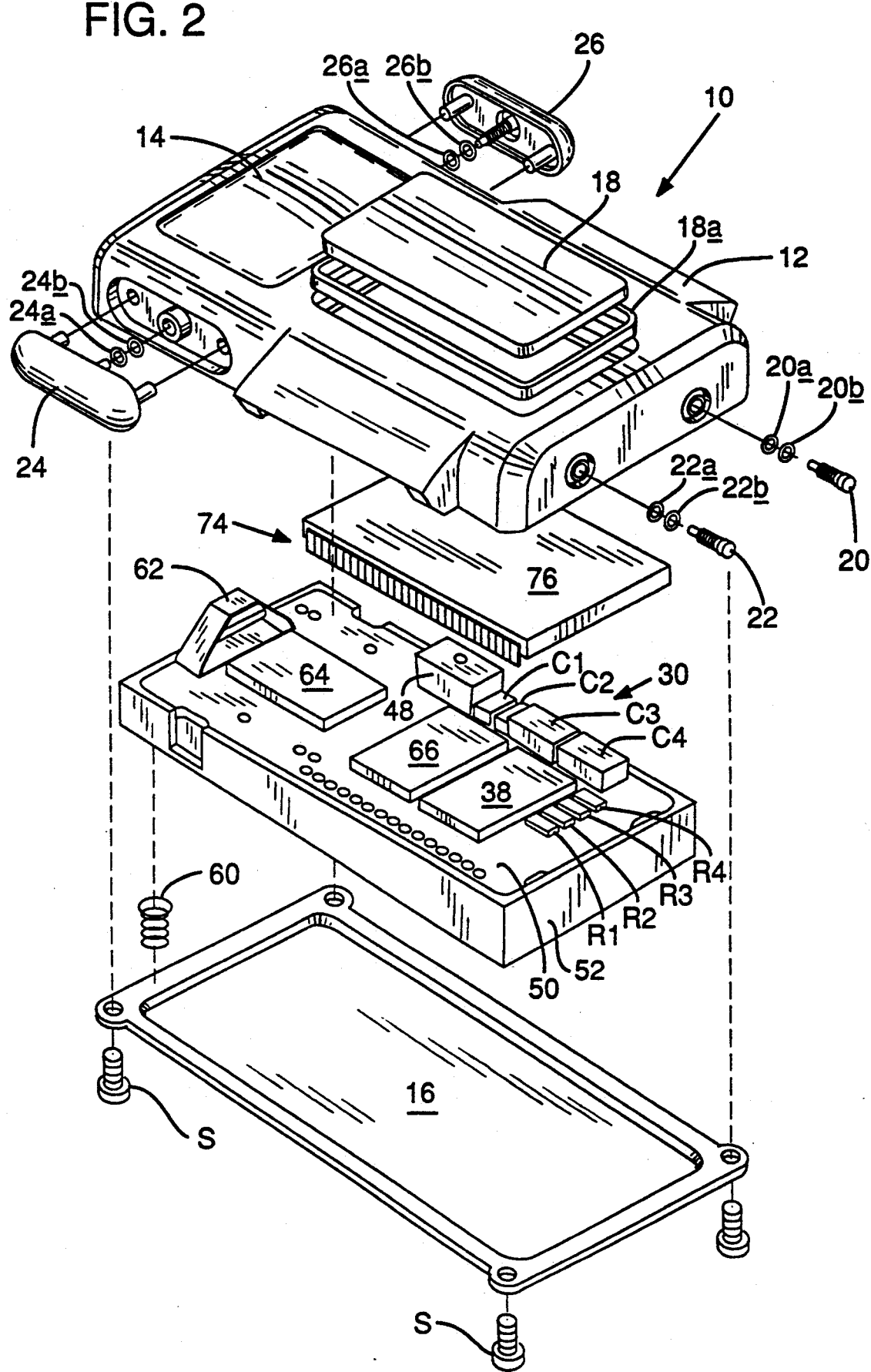
FIG. 2 is an exploded frontal isometric view of the ECG monitor corresponding with that of FIG. 1, with the wrist band removed for clarity.

Referring now to FIG. 2, apparatus 10 is shown in exploded isometric view. Wrist-worn ECG, or cardiac data, monitoring apparatus 10 comprises a housing 12 including first and second dry skin electrodes 14, 16 unitarily connected therewith and forming an integral part thereof for making conductive contact with a cardiac patient's skin surface and a bezel 18 (with associated gasket 18a) also forming an integral part thereof; plural pushbutton switches 20, 22, 24, 26 (with associated O-ring gaskets 20a, 20b, 22a, 22b, 24a, 24b, 26a, 26b); a conventional watchband 28 of any suitable size and structure (see FIG. 1); and, entirely contained within housing 12, electronics indicated generally at 30.

Figure 4:
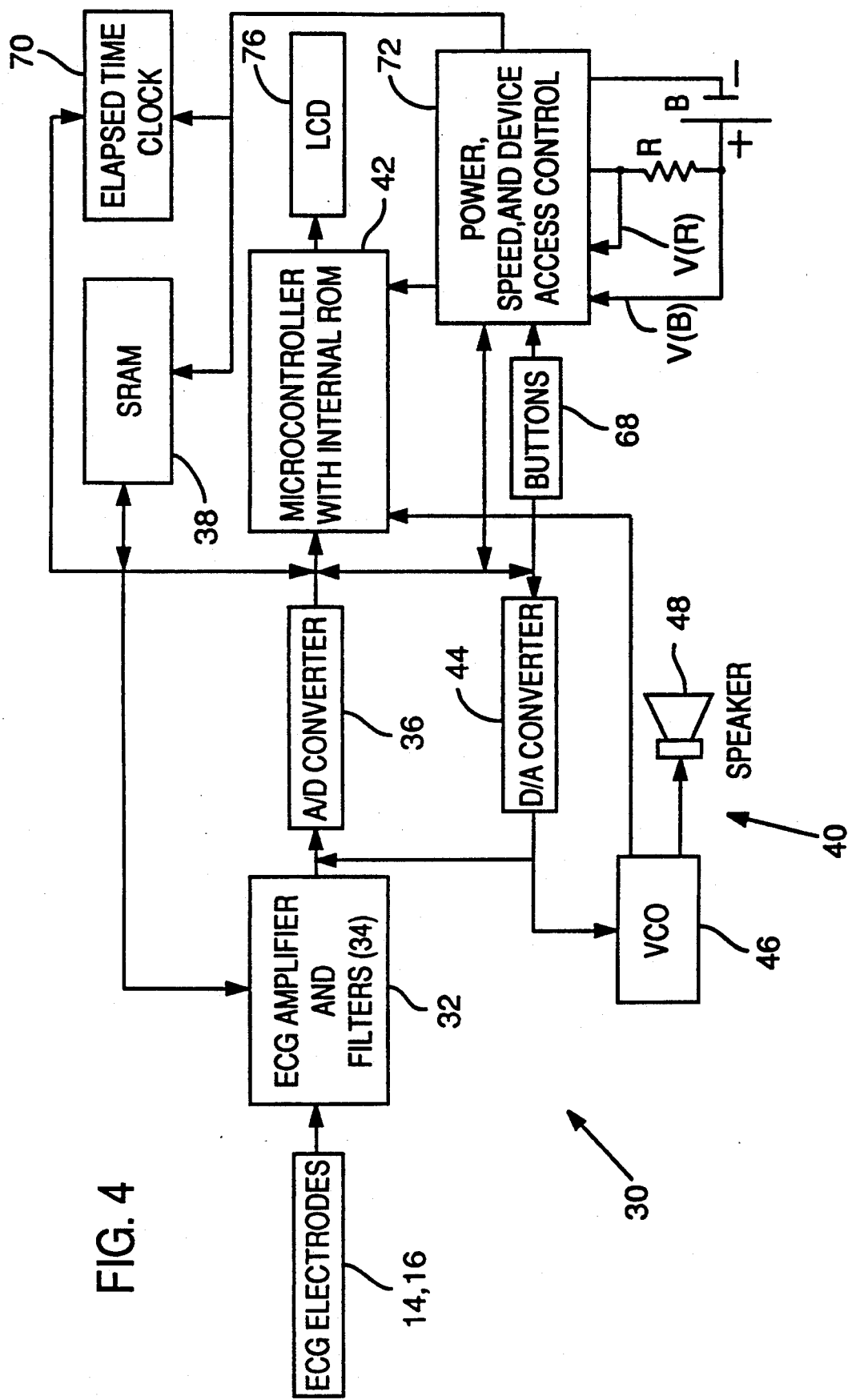
FIG. 4 is a schematic block diagram of the monitor shown in FIG. 1.

Turning briefly to FIG. 4, electronics 30 include an ECG signal amplifier 32 including hardware filters 34 coupled with electrodes 14, 16 for producing an analog signal representative of the electrical field on the surface of the patient's skin and between electrodes 14, 16. Electronics 30 also include analog-to-digital signal conversion means, or analog-to-digital converter (ADC), 36 connected with amplifier 32 for producing digital data representing the patient's ECG waveform over a predefined interval of time. Electronics 30 preferably include 32-kilobytes (32-kb) of static read-and-write memory (SRAM) 38 that operates as means for recording digital data produced by ADC 36. Electronics 30 also include means 40 (preferably including a microcontroller with 8-kb of read-only memory (ROM) 42, a digital-to-analog converter (DAC) 44, a voltage-controlled oscillator (VCO) 46 and a speaker 48) for wirelessly, and preferably audibly, communicating data recorded in SRAM 38 to a remote site for verification or so-called "over-read", real-time diagnosis and/or archival recording.

Because in its preferred embodiment wrist-worn cardiac data monitor 10 comprises electronics 30 providing at least all of the functions described immediately above, an extremely high level of functional density is achieved by the invention. By functional density is meant a measure of the functionality per unit volume, whether the volume is that contained within housing 12 or is that contained within and including housing 12 (of which electrodes 14, 16 form an integral part: electrode 14 integrally molded therein and electrode 16 by the use of screws S turned into corresponding tapped holes formed therein). In accordance with the preferred embodiment of the invention, and as measured by conventional water displacement means, the interior, or contained, predetermined volume within housing 12 does not exceed approximately 0.75 -inches$^3$, and is preferably equal to or less than approximately 0.625-inches$^3$. Similarly measured, the exterior predetermined volume within and including housing 12 (and integral electrodes 14, 16 and bezel 18) does not exceed approximately 1.5-inches$^3$, and is preferably equal to or less than approximately 1.25-inches$^3$.

Figure 3B:
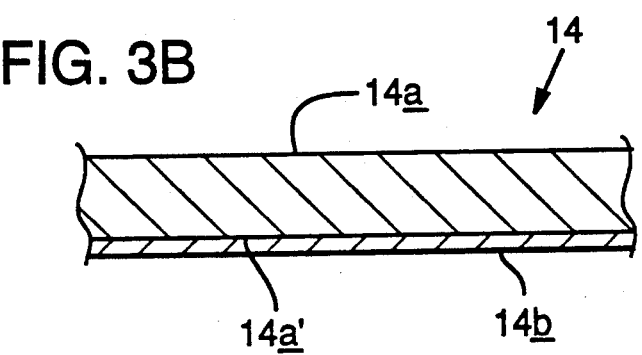
FIG. 3B is an enlarged, fragmentary cross-sectional view of the lower electrode shown in FIG 3A.

Dry skin electrodes 14, 16 are designed for use with equipment capable of producing or monitoring changing electrical conditions (indicative of changing cardiographic conditions) at the surface of a patient's skin, and are particularly suitable in cardiac monitoring, e.g. by apparatus 10. As illustrated in FIG. 3B, an electrode such as electrode 14 preferably comprises an expanse 14a formed of a base metal such as stainless steel, with expanse 14a being electrically connectable with such monitoring equipment, as illustrated in FIGS. 1 and 2. Plating an outer, skin-contactable region or surface 14a' of expanse 14a is a composition 14b (shown in greatly enlarged thickness in FIG. 3B relative to that of expanse 14a) including a first component of a preferably biocompatible, conductive (e.g. metallic) element such as titanium, and at least a second component chosen from a group including nitrogen and carbon. It will be understood that electrode 16 of apparatus 10 is of identical material content and cross-sectional structure as electrode 14, but is of much greater surface area.

Those of skill in the arts will appreciate that such electrode 14 might be connectable with stimulus/response equipment by any suitable means including an electrical conductor or wire, e.g the coil spring used in connection with apparatus 10 having such electrode 14 integrally housed therewith. Those skilled also will appreciate that such electrode 14 comprising such plated expanse obviates use of a messy, conductive gel, and even the so-called "residue-free", self-adhesive gelatinous pads that often are used to enhance conductivity between an electrode and a patient's skin. Finally, those of skill in the arts will appreciate that stimulus/response equipment with which such invented electrode 14 is believed to be useful includes not only electrical conditions change-monitoring, or response, equipment but also electrical conditions change-producing, or stimulus, equipment such as neural, muscular or other anatomical electrostimulation equipment.

Preferably base metal-plating composition 14b is in order of preference a titanium nitride (TiN), titanium carbide (TiC) or titanium carbo-nitride (TiCN) layer approximately 3-microns (0.003-inch) thick. Such composition can be plated by known chemical or physical vapor deposition techniques, and preferably the plating composition is polished to a smooth finish primarily for aesthetic reasons. Such plating of base metal expanse 14a has been found to protect, and thus to greatly extend the life, of a dry skin electrode such as electrode 14 by producing an extremely hard, exterior, skin-contactable surface. Such plating also has been found to provide high conductivity and thus to produce a high quality electrical interface between an electrode such as electrode 14 and the patient's skin surface, which may be very dry.

Figure 3A:
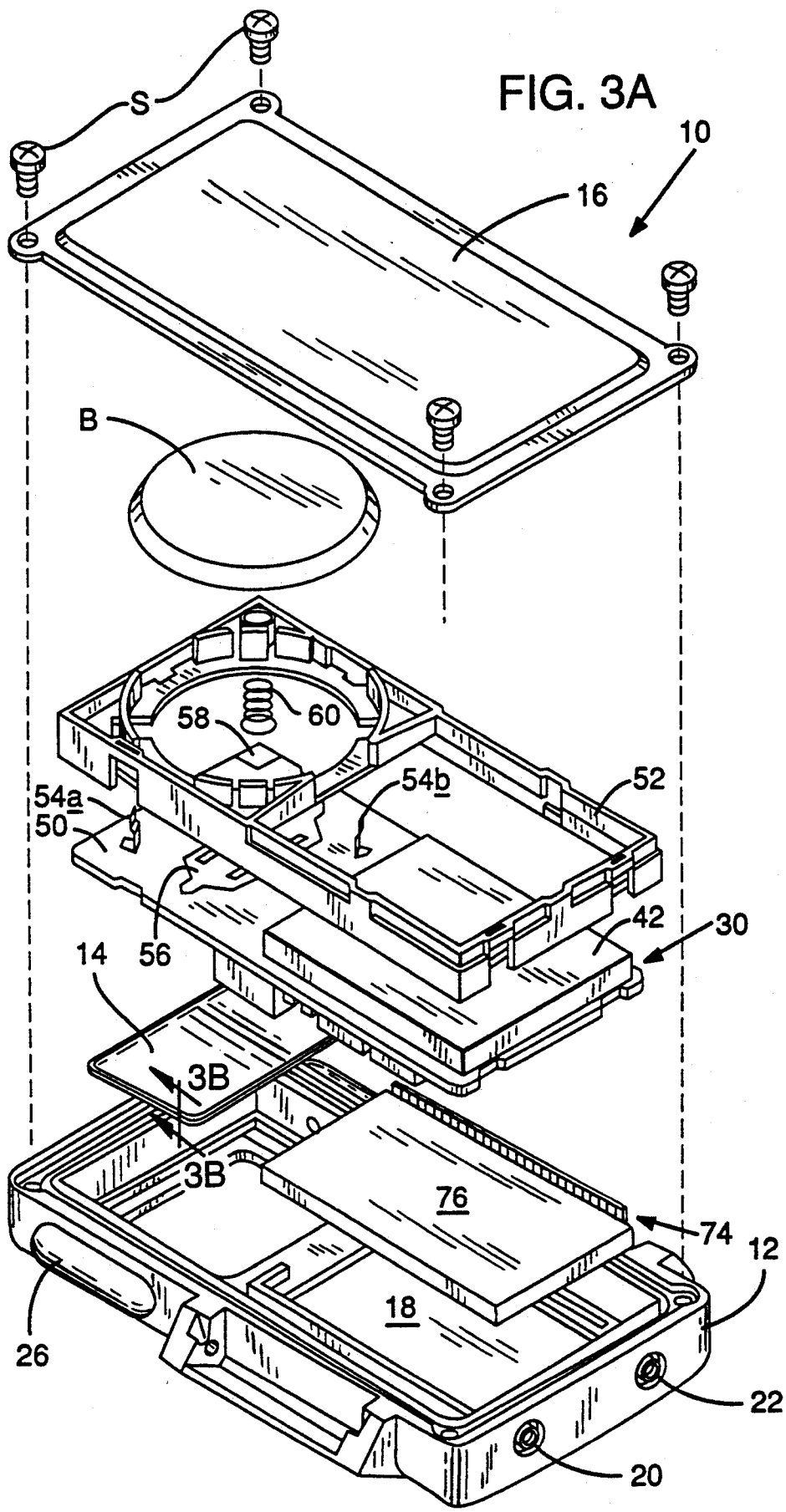
FIG. 3A is an exploded isometric view of the ECG monitor corresponding with that of FIG. 2, but showing it generally from the rear instead of the front.

Referring now briefly to FIGS. 2 and 3A, necessary details of the structure of apparatus 10 made in accordance with its preferred embodiment will be described. Electronics 30 may be seen to be implemented preferably in various discrete and integrated circuits surface-mounted or ultrasonic wire bonded onto a multi-layer printed circuit board (PCB) 50 supported within housing 12 by a perimeter support member 52. Thus, PCB 50, which preferably comprises plural adhered, copper-clad epoxy layers, may be seen physically to mount and interconnect the various circuitry shown schematically in FIG. 4, including on its bottom side a microcontroller (with integral ROM) chip 42, interconnecting and mounting support members 54a, 54b for connection with one terminal of battery B, a double-leaf spring member 56 for connection with the other terminal of battery B and a "land", or circuit pad, 58 for connecting lower electrode 16 via a coil spring 60 to one signal input terminal of ECG amplifier 32.

Upper electrode 14 is connected to the other signal input terminal of ECG amplifier 32 via a generally trapezoid-shaped, split and thus slidably yielding, leaf spring 62 connected to a circuit pad formed on the top side of PCB 50. In the preferred embodiment of the invention, ECG amplifier 32, including associated hardware input signal filters 34, are implemented in a custom analog chip-on-board (e.g. a so-called application-specific integrated circuit, or ASIC) 64, which is mounted on PCB 50 by known ultrasonic wire-bonding techniques. A custom digital (ASIC) chip-on-board 66 implements ADC 36, DAC 44, VCO 46, pushBUTTONS logic 68, an elapsed-time clock 70 and POWER, SPEED and DEVICE ACCESS CONTROL logic 72 (refer briefly to FIG. 4). Custom analog and digital chips 64, 66 may be formed on conventional substrates, may have any desired layout as determined by speed/power requirements and conventional VLSI chip design rules and tools.

Yet another VLSI chip, which is surface-mounted on the top side of PCB 50, is SRAM chip 38. Preferably connected to the top side of PCB 50 via a so-called "Zebra" elastomeric strip (or other flexible connector means) 74 is a custom-masked liquid crystal display (LCD) chip 76, which upon assembly of apparatus 10 lies above neighboring digital chip 66 and SRAM 38 and directly below bezel 18. As will be seen by reference to the operational description provided herein, conventional chronometric, as well as cardiac monitoring and other status information, are provided by selectively activating masked segments of LCD 76 to provide visible alphanumeric, graphic and symbolic indicia of the operation of apparatus 10.

The remaining circuitry of electronics 30 preferably is mounted, as better shown in FIG. 2, to the top side of PCB 50. Such circuitry includes speaker 48, relatively smaller decoupling capacitors C1, C2, relatively larger decoupling capacitors C3, C4 and resistors R1, R2, R3, R4. It will be understood by those skilled in the arts that external capacitors C1 and C2 are too large to be integrated into the VSLI chips, and that external resistors R1, R2, R3, R4 (one of which is the physical embodiment of current sense resistor R shown in FIG. 4) are either precision resistors that cannot be so integrated or resistors the values of which are application or operational mode specific in the use of apparatus 10. For example, certain of the external resistors are used to establish voltage or frequency response thresholds of ECG amplifier 32 and filters 34, and advantageously are provided external to the VSLI chips so that such operational parameters easily may be changed.

Importantly enabling the achievement of unprecedentedly high functional density in a wrist-worn cardiac monitor, along with the electrical and physical partitioning and packaging design described above, is the design of speaker 48. Speaker 48 generally is of the type used in hearing aids and pagers, but is customized for its application in means 40 for audibly communicating ECG data to a remote site preferably over a voice channel, e.g. telephone lines, without the need for external connection or transmitter. Speaker 48 is characterized in that it provides preferably approximately 83-decibels (83-db) sound pressure at approximately 1-inch, and a relatively flat response preferably between approximately 1-kHz and 3-khz.

These attributes enable speaker 48 to deliver to a conventional telephone microphone or equivalent transducer for transmission over telephone lines the required audio tones, which preferably are a frequency-shift keyed (FSK) signal at frequencies of approximately 1.5-kHz and 2.5-kHz for the pulse, date and time markers, and a frequency modulated (FM) carrier for the digitized ECG data representing the patient's cardiography. Such a speaker, or what is referred to as a "hearing aid receiver" is available, for example, from Knowles, Inc. of Franklin Park, Ill., but of course other sources may be suitable. Preferably, apparatus 10 is rendered water-resistant, despite the provision in housing 12 adjacent speaker 48 of three slotted speaker holes, or speaker grill, 12a, by affixing a small patch of water-impermeable but air-permeable material such as Gortex ® fabric to the inside surface of housing 12 (not shown in FIGS. 2 and 3A, for the sake of clarity).

In accordance with the preferred embodiment of the invention, analog chip 66 includes not only ECG amplifier 32 and associated hardware filters 32, but also digital logic circuitry that permits microcontroller 42 programmably to select various operational parameters. For example, analog chip 66 includes gating circuitry for controlling the gain, common-mode rejection ratio (CMMR) and DC offset/zeroing of amplifier 32, as by digital potentiometer design techniques used in various applications. e.g. cathode ray tube (CRT) monitors. Analog chip 66 also includes gating circuitry for controlling the upper and lower bandpass frequencies of filters 34, as by selectively switching capacitors into and out of the filter circuit. Those of skill in the arts will appreciate that, because it includes both analog and digital circuitry, analog chip 66 is preferably partitioned internally to protect the relatively noise-sensitive digital circuitry from the relatively noise-productive analog circuitry.

Those skilled in the arts will appreciate that the illustrated and described partitioning and physical packaging of apparatus 10, and particularly of electronics 30, achieves the extremely high functional density acclaimed herein, although it is possible that alternative device selection and circuit topology, partitioning and/or packaging schemes might be used within the spirit of the invention. Those of skill also will appreciate that in accordance with the preferred embodiment, housing 12 and support member 52 are molded plastic such as acrylonitrile-butadiene-styrene (ABS), which renders apparatus 10 extremely rigid and durable, but also lightweight and relatively inexpensive to manufacture.

Returning to FIG. 4, a schematic block diagram of the invention is shown that illustrates means by which the various power management, chronometric, ECG signal conditioning and digitizing, demand data recording and trans-telephonic communication functions are performed. Those skilled in the art will appreciate that the illustrated circuit structure, by the preferred embodiment of the invention, is contained entirely within housing 12 of apparatus 10, with the exception of course of electrodes 14, 16, which it may be seen from FIG. 1 form an integral, unitary part of housing 12.

In operation, apparatus 10 is worn on the wrist of the cardiac patient much like a conventional wrist watch. In the embodiment of the invention shown in FIG. 1, wrist-worn cardiac monitor 10 would be worn on the left wrist, yielding access by the patient to pushbuttons 20, 22, 24, 26 by the right hand and visibility to the patient of LCD 76. With apparatus 10 thus positioned on the left wrist, the palm of the right hand easily can be placed into contact with upper electrode 14, thus impressing between upper electrode 14 and lower electrode 16 a signal representative of the patient's cardiography (as indicated by a varying electrical potential at the patient's skin surface). When the recording of a cardiac waveform is desired, the patient merely depresses pushbutton 26, effecting so-called "demand"

recording of what may prove to be an arrhythmic cardiac waveform representing an abnormal cardiac "event."

Continuously, microcontroller 42 monitors pushbuttons 20, 22, 24, 26 for even momentary closure, via pushbuttons logic 68 and power, speed and device access control 72. Upon the depression of pushbutton 26, microcontroller 42 supplies power to ECG amplifier 32 and to ADC 36 and then delays a few, e.g. approximately five, seconds. This timeout provides time for the user to position his or her palm on upper electrode 14 and for the ECG signal to stabilize.

After the delay, microcontroller 42 stores, or captures, ECG data input via ECG electrodes 14, 16, ECG amplifier 32 and ADC 36 in SRAM 38 as a cardiac data record. Such a stored ECG data record is available for immediate or delayed playout, e.g. transtelephonic or other telecommunication, to a remote site. Importantly, pushbutton 26 is monitored to begin such ECG data recording at all times, even if the patient is in the process of initializing chronometric functions, e.g. setting the date, day or time. This "override" feature of apparatus 10 assures no loss of ECG data even when there is a cardiac event worthy of recording that happens to coincide with the patient's other uses of apparatus 10.

Those skilled in the arts will appreciate that apparatus of the invention made in accordance with its preferred embodiment described above provides unprecedented functional density in an integral, wholly self-contained, compact and lightweight, wrist-worn package, the functionality including the ability to produce ECG data records on demand and to play the same back to a remote site with the use only of a touch tone telephone or other suitable audio communication channel. It further will be appreciated that, with the addition to apparatus 10 of one or more input signal jacks, one or more pairs of external electrodes also or instead may be monitored to produce ECG data independent upon the detection of a cardiac event, i.e. based not upon patient demand but upon continuous or periodic monitoring of the patient's cardiography and comparing the same to predetermined ECG signal criteria.

As described and illustrated in U.S. Pat. No. 4,958,641 entitled "Heart Monitoring Method and Apparatus", issued Sep. 25, 1990 and having a common assignee with the present invention, event determination and automatic windowed data recording means may be included within apparatus 10. Similarly, as described and illustrated in our U.S. Pat. No. 5,012,814 entitled "Implantable-Defibrillator Pulse Detection-Triggered ECG Monitoring Method and Apparatus", issued May 7, 1991, pacemaker or implantable cardioverter/defibrillator monitor (ICDM) pulse detection means may be included within apparatus 10. The teachings of these patents are incorporated herein by this reference, and the provision in apparatus 10 of what will be referred to generally as pulse monitoring capability is described below in general terms that assume familiarity with such patent teachings.

Generally, such inclusion requires simply providing supporting firmware in the integral ROM of microcontroller 42, designed in accordance with the teachings of the patents mentioned above and also designed properly to program the programmable hardware filter and amplifier operational parameters discussed herein. For example, for pacemaker or ICDM pulse detection, the hardware filter through which the patient's skin potential- or cardiography-representative analog input signal is passed typically might have a 0.5-Hz lower cutoff frequency and a 100-Hz upper cutoff frequency, rather than the typically 0.5-Hz lower and 30-Hz upper cutoff frequencies of the filters as they are programmed in accordance with the preferred embodiment in which apparatus utilizes integral electrodes 14, 16 and is optimized for monitoring ECG signals for a patient having neither pacemaker nor ICDM (e.g. the required cardiography bandwidth for a cardiac patient with a pacemaker is somewhat wider than for one without because finer ECG data resolution is desired).

For detection of the relatively fast pacemaker-produced and/or ICDM-produced pulses, the hardware and digital filters might be bypassed, e.g. by a jumper wire or programmable gate, and a hardware pacer or ICDM pulse detector circuit (similar to that described in our U.S. Pat. No. 5,012,814) used to produce a trigger signal the duration of which is analyzed by microcontroller 42 of apparatus 10 for "marking" the time-associated ECG data record. In both of these alternative embodiments, the pulse detection circuitry is integrated preferably within analog chip 64 and there is provided in connection with housing 12 a miniature external jack to accommodate external electrodes (e.g. for a two conductor miniature phono plug). Such even further increases the functional density of apparatus 10.

It will be appreciated that, in the case of pacemaker-produced pulse detection, typically the input signal would need to be amplified, e.g. by preferably approximately 100×, prior to being characterized in accordance with the patent teachings. This is because typical pacemaker-produced pulses are of much lesser amplitude than typical ICDM-produced pulses. It will be appreciated that such detector as is described in detail in the referenced patents, suitably modified as necessary to detect either pacemaker pulses or ICDM pulses, or both, is referred to herein in the most general sense as means for detecting a pulse produced by an implanted pacemaker or defibrillator and for recording with an associated ECG data record an indicium of the occurrence of such pulse.

With this understanding of the invention, now wrist-worn monitor 10 may be seen to include, in addition to housing 12 and electrodes 14, 16, a detector, or ECG amplifier 32 having hardware filters 34, for detecting cardiac activity represented by variations in the surface potential of the patient's skin and for producing an ECG signal; an analog-to-digital signal converter, or ADC 36, operatively connected with the detector and responsive to the ECG signal for producing ECG data; means coupled with the converter for determining that a cardiac event has occurred, the determining means producing a trigger signal; a recorder, or SRAM 38 controlled by microcontroller 42, responsive to said trigger signal for recording selected ECG data proximate in time to such cardiac event; and a transmitter, or data-communicating means 40, integrally and intimately connected therewith and substantially completely contained therein for communicating the recorded ECG data to a remote site.

It will be understood that such cardiac event-determining means broadly includes a patient-actuated record switch 26 or such automatic event determination means as is described in U.S. Pat. No. 4,958,641. It also will be understood that cardiac event broadly refers to such regularities as a pacer pulse, an ICDM pulse, as well as other ECG signal attributes that meet predetermined criteria, e.g. bradycardia, tachycardia or ischemia.

It will be appreciated that LCD 76 is used in accordance with the preferred embodiment for many purposes including the display of conventional day, date and time, as well as cardiac monitor-specific indicia of the patient's ECG activity. Myriad uses of LCD for providing visual indicia to the patient of either cardiographic or monitor status information may be provided. For example, the patient's pulse might be indicated by a pulsating heart symbol, thereby enabling visual ECG activity monitoring by the cardiac patient. Other indicia produced by controller means including microcontroller 42 and LCD 76 contained within the predetermined volume defined by housing 12 are possible, with nearly limitless variation. For example, actual cardiac waveforms (whether QRS complex or pacer pulse, or both) might be displayed as a lower resolution version of the digital ECG data records stored in SRAM 38 by microcontroller 42. All such waveform-interpreting and display-producing controller means contained also within the compact housing of wrist-worn cardiac monitor 10 are within the spirit of the invention.

Returning now to a discussion of the preferred embodiment of the invention, apparatus 10 has the capacity to record approximately five minutes of ECG data, which typically would represent multiple cardiac events. Microcontroller 42 is programmed in accordance with known techniques to manage such multiple ECG data records in SRAM 38, including marking each one with a time of day indication by use of elapsed-time clock 70. Preferably, elapsed-time clock 70 keeps track not only of the actual time of day entered by the cardiac patient via pushbuttons 20, 22, but also the relative, elapsed time since apparatus 10 first began recording. Thus, even if the patient has not set the time of day, or has set it incorrectly, nevertheless all recorded ECG data will be marked with an indication of when the event that it represents occurred.

When it is desired to transmit the recorded ECG data to a remote site for diagnosis or archival recording purposes, the patient need only dial the phone number of the diagnostic center, await an indication that a connection has been made and momentarily depress pushbutton 24, e.g. with the thumb of the right hand. Automatically, microcontroller 42 reads records from SRAM 38, formats them in accordance with a predetermined byte-serial protocol and causes one or more records to be transmitted as an FM (modulated) carrier via DAC 44, VCO 46 and speaker 48. Microcontroller 42 is programmed to be fault tolerant: If pushbuttons 24, 26 are depressed at the same time, then any temporarily stored ECG data record is transmitted, and if there is no stored ECG data record, then the ambiguous command is interpreted as a record command such that present ECG waveform data is stored in SRAM 38.

Figure 5:
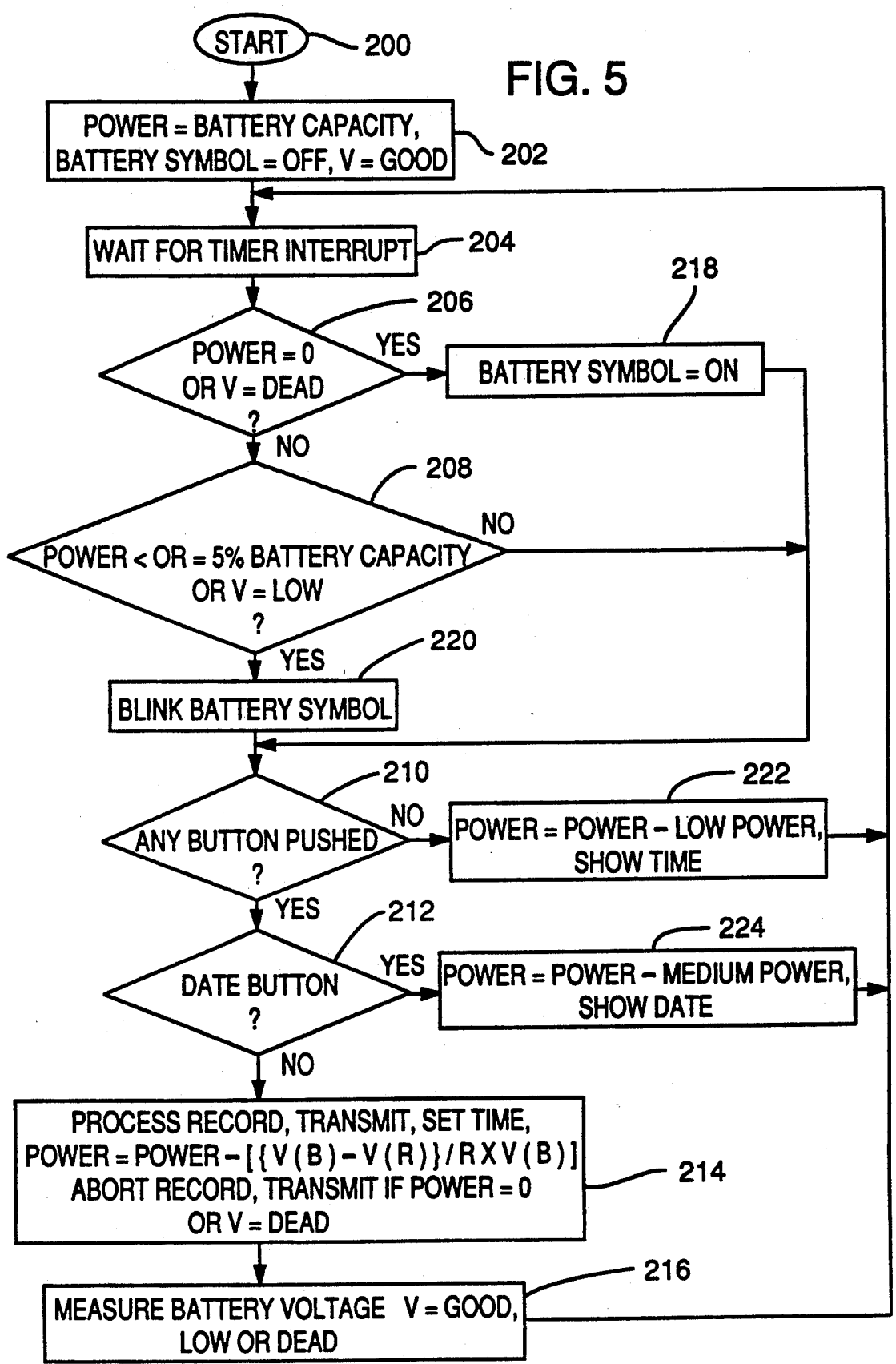
FIG. 5 is a flowchart illustrating the battery life prediction method of the invention.

Referring next to FIG. 5, a preferred method of the invention by which battery end of life is predicted to avoid inadvertent loss of ECG data in a wrist-worn monitor such as that of apparatus 10 is described by reference to a flowchart. The preferred method comprises the steps of 1) predetermining a power capacity value for such battery; and periodically thereafter 2) measuring the current drain on such battery while such monitor is being supplied with power therefrom, 3) calculating the power being consumed by such monitor based upon the measuring, and 4) comparing the result of the calculating with the first power capacity value; then based upon the comparing, 5) determining that the consumed power is approximately equal to the power capacity value; and 6) annunciating on such monitor the impending end of life of such battery.

The power capacity value-predetermining step is illustrated, at the START 200 of the firmware routine, as including loading a variable POWER with a predetermined BATTERY CAPACITY value (based, for example, upon published watt-hour specifications for battery B), initializing a boolean variable BATTERY low SYMBOL with a value representing that it is OFF and initializing a voltage merit variable V with a value representing that it is GOOD. These preliminary steps are indicated by task block 202.

Periodically, as determined by WAITing FOR a fixed-interval TIMER INTERRUPT at task block 204, the following steps are taken. At decision block 206 it is determined whether either of two first conditions prevails: assuming that neither POWER is equal to 0 nor battery B voltage V is equal to DEAD, then at decision block 208 it is determined whether either of two second conditions prevails: assuming that neither POWER is less than or equal to 5-% of the BATTERY CAPACITY nor V is equal to LOW, then decision block 210 is reached. At 210, 212 it is determined whether ANY BUTTON has been PUSHED and, if so, whether it was the DATE BUTTON.

If the button pushed was not the DATE BUTTON, then at task block 214 the ECG DATA RECORD is PROCESSed and TRANSMITted; the TIME of day is SET and the current drain on battery B is measured (while ECG data monitor apparatus 10 is being supplied power therefrom). This distinctive current drain measurement step is performed in accordance with the preferred method by measuring the voltage V(B) on the positive terminal of battery B and also measuring the voltage V(R) at a series-connected sense resistor R of known value. After both voltage measurements are taken, the current drain on battery B, which is equal to the current through sense resistor R, is determined by evaluating the expression $(V(B) - V(R))/R$. The power being consumed by ECG data monitor 10 is calculated, based upon the current-measuring step, by multiplying the current drain on battery B, as previously determined, by V(B). This consumed power value is subtracted from POWER, thereby effectively comparing the result of the consumed power calculation step with the BATTERY power CAPACITY to produce a remaining POWER estimation or prediction value.

A difference of zero (POWER=0) that results from this comparing step indicates that the consumed power is approximately equal to the POWER CAPACITY value. Of course, even if POWER≠0, but if battery voltage V(B) is less than a predefined minimum operating threshold voltage for apparatus 10, such that battery B is nominally DEAD, then the recorded ECG data potentially has been corrupted. In this case at task block 214 any ECG data recording and any transmission in progress are aborted. At 216 battery voltage V again is measured to ensure the periodic currency of the battery voltage variable. As may be seen, upon the next timer interrupt if it was at 214 determined, based upon the consumed power calculation step, that V=DEAD or that the consumed power is approximately equal to the POWER CAPACITY value (POWER=0), then at 218 the BATTERY SYMBOL on LCD 76 of ECG data monitor 10 is turned ON, thereby preferably visibly annunciating on such monitor the impending end of life of battery B. Those skilled in the arts will appreciate that any form of annunciation is within the spirit of the invention.

Still referring to FIG. 5, if it is determined at decision block 208 that POWER is less than or equal to 5-% of BATTERY CAPACITY, then at task block 220 the BATTERY SYMBOL on LCD 76 of ECG data monitor 10 is BLINKed. If at decision block 210 it is determined that there was not ANY BUTTON PUSHED, then at task block 222 POWER is reduced by the value of a constant LOW POWER, and LCD 76 of ECG data monitor 10 SHOWs the TIME of day. Finally, if it is determined that it was the DATE BUTTON which was pushed, then at task block 224 POWER is reduced by the value of a constant MEDIUM POWER, and LCD 76 of ECG data monitor 10 SHOWs the DATE. Thereafter, control returns to WAIT FOR TIMER INTERRUPT 204.

It may be seen now by reference to FIG. 5 that the preferred battery end of life prediction method may be described as follows: First, a power capacity value for battery B is determined, e.g. by reference to its nominal operating specifications, and stored in memory such as SRAM 38 by microcontroller 42. Repeatedly thereafter and at a predetermined rate based, for example, on a 1/8th-second timer interrupt at task block 204, (1) the current drain on the battery is measured, e.g. by microcontroller 42 while the ECG data monitor is supplied power from the battery; (2) the instantaneous power being consumed by the monitor based on such measuring is calculated; and (3) the result of the calculation is compared with the predetermined power capacity value by microcontroller 42.

Second, based upon the comparison, it is determined whether the power so far consumed is approximately equal to the predetermined power capacity value. If so, then third, the impending life of battery B is annunciated on ECG data monitor 10, e.g. by activation of an LCD 76 segment such as a "LOW BATTERY" text or graphic symbol or by turning on an audible alarm as by producing a beep on speaker 48. It will be appreciated that any form of annunciation may be used, and that alternative methods of predicting the end of life of battery B may be used. For example, within the spirit of the invention, a variable POWER CONSUMED might be initialized to zero and the calculating step might increment, rather than decrement the variable, to represent the accumulated total power consumed rather than the total power remaining, with the comparing step comparing the POWER CONSUMED variable to the predetermined BATTERY CAPACITY rather than to zero.

Other variations will also be effective in functioning to ensure that ECG data is not corrupted by a low power condition of apparatus 10, that the patient is forewarned prior to the loss of valid ECG data that such should be tele-transmitted or it may be lost and that the patient is informed of an appropriate time to change battery B. Clearly, the most conservative measures must be taken in order to prevent power or data loss in this critical patient care application. Yet, in accordance with the invention, such prevention is accomplished without unnecessarily limiting the utility of apparatus 10 by measuring actual current draw on the battery, which is based in turn upon the demand the patient places on apparatus 10, rather than by some arbitrary and perhaps inaccurate assumptions of use rates.

The invented battery end of life prediction method and its included battery current draw measuring technique are particularly useful in a wrist-worn cardiac monitor because they so greatly extend the useful monitoring period. With longer-lived batteries that may be used with apparatus 10, it is expected that the above-described operation may be altered such that ECG data monitoring begins immediately upon the positioning of the patient's palm in stable contact with electrode 14, without the need for the patient to depress pushbutton 26. While consuming more power because amplifier 32 and ADC 36 would be supplied with power a larger percentage of the time, nevertheless such operation would yield the advantage that the patient would not be required to depress a button in order to record his or her cardiography. It is envisioned to be within the spirit of the invention that higher capacity batteries and lower power integrated circuit technologies will render such event determination-based or semi-automatic, rather than demand-based or volitional, operation feasible and perhaps desirable.

Figure 6:
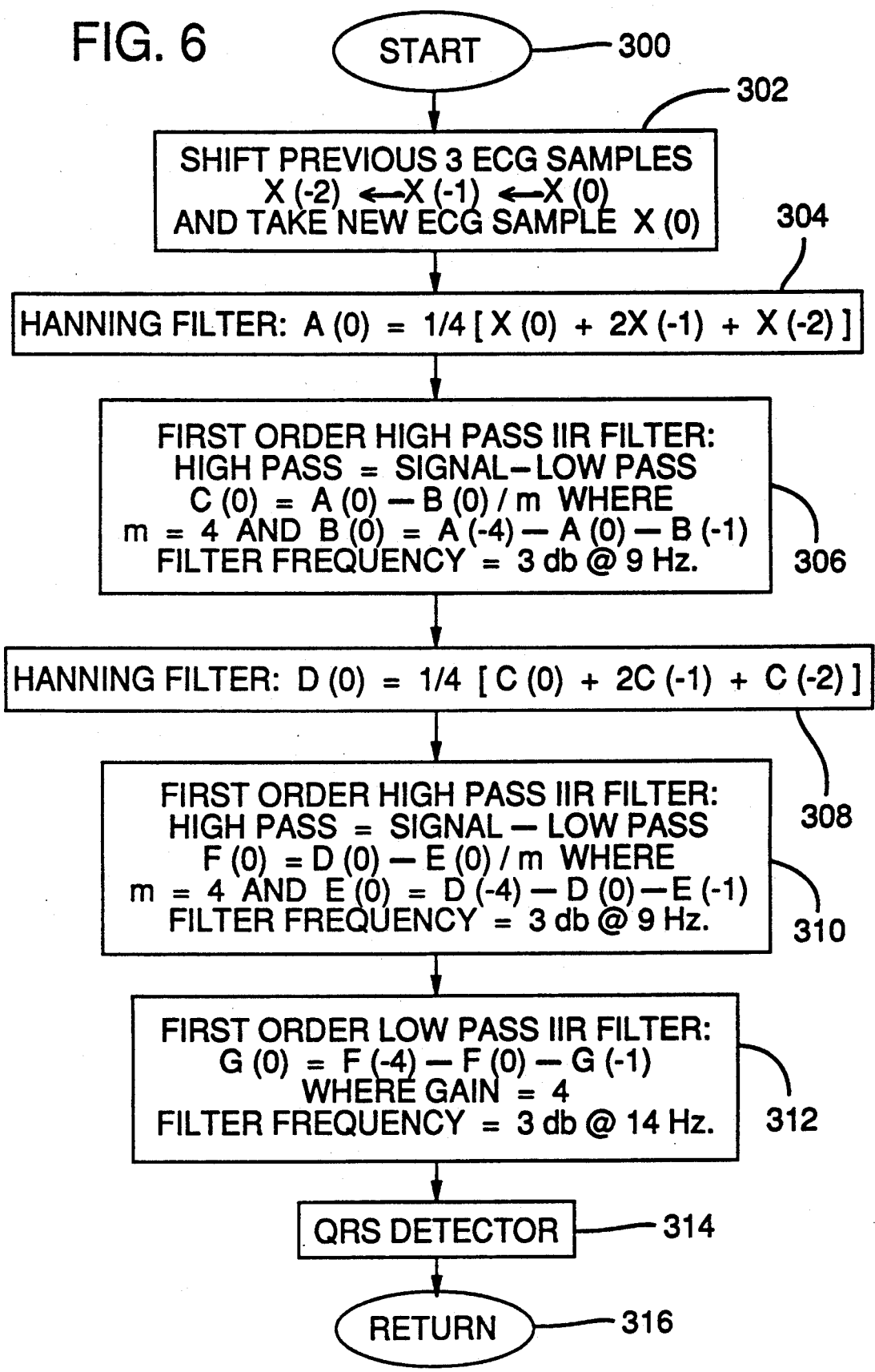
FIG. 6 is a flowchart illustrating the digital filtering method of the invention.

Referring now to FIG. 6, a preferred method of the invention by which ECG data digitally is filtered by apparatus 10 is described by reference to a flowchart. The preferred method is illustrated as beginning at START point 300. At task block 302 the oldest of three previous ECG samples, $X(-2)$, is discarded and the more recent two thereof, $X(-1)$ and $X(0)$, are shifted in an ECG digital data array, or temporary buffer memory area of SRAM 38, to make room for a new ECG sample, which goes into the $X(0)$ data cell. At task block 304 the digital data is digitally filtered by passing it through a Hanning filter that evaluates the expression $$A(0) = \tfrac{1}{4}[X(0) + 2X(-1) + X(-2)] \qquad (1),$$

where $X(0)$ is a current ECG data sample, $X(-1)$ is an immediately preceding ECG data sample, $X(-2)$ is an ECG data sample immediately preceding the $X(-1)$ ECG data sample and $A(0)$ is the output value of the digital filter.

Those of skill in the arts will appreciate that expression (1) is a particular instance of the more general expression $$A(0) = 1/m[X(0) + nX(-1) + X(-2)] \qquad (2),$$

which itself may be more generally expressed $$A(0) = m^{\pm 1} \sum_{p=-q}^{0} nX(p), \qquad (3)$$

where $X(p)$ is understood to be one instance of the succession of ECG data samples produced by the sampling and where $A(0)$ is the output value produced by said evaluating. Preferably, as may be seen from expression (1), m is an integer power of two, n is zero or an integer power of two, p is a negative integer or zero and q is an index identifying the number of the sample under consideration (o intentionally is omitted in the expressions and illustrations for the sake of clarity).

Importantly, the coefficients of any added terms, as well as the other multiplier used in evaluating the above expressions, are integer powers of two. This feature makes expression evaluation in a digital system very straightforward, and completely obviates in such a system time- and space-consuming floating point arithmetic: Multiplying or dividing a digital value by a number that is a power of two can be accomplished by simply shifting the value right or left by a number of bits that is equal to the power of two by which the value is to be multiplied or divided. For example, the middle term of the sum in expression (1) can be multiplied by two by simply shifting the digital representation of X(−1) left one bit, and the sum itself can be divided by four by simply shifting the digital representation of X(0)+2X(−1)+X(−2) right two bits.

It is not adequate simply to choose coefficients and other multipliers and divisors that are integer powers of two, without then choosing a digitizing sample rate that achieves the desired filtering effect. In accordance with the preferred embodiment and method of the invention, the ECG signal sampling rate is approximately 109-Hz, which along with the coefficient selection that is described and illustrated herein has been found empirically to produce very effective digital filtering of the ECG analog signal that, after hardware pre-filtering which preferably is a part of amplification (see filters 34 of ECG amplifier 34 in FIG. 4), is produced by dry skin electrodes 14, 16.

Referring still to FIG. 6, at 306 the Hanning filtered (smoothed) ECG data is further processed by a first order, high-pass infinite impulse response (IIR) filter that effectively produces 3-decibel (3-db)/decade rolloff at 9-Hz, a frequency below which it has been found that pertinent QRS complex data is not present. The processing at task block 306, in accordance with the preferred method of the invention, involves evaluating the expression $$C(0)=A(0)-B(0)/m \qquad (4),$$

where m=4 and where $$B(0)=A(-4)-A(0)-B(-1) \qquad (5),$$

wherein of course A(p) are present and previous outputs of the first Hanning filter implemented at task block 304 and wherein B(−1) is the previous output of the present IIR filter implemented at task block 306. Again, it is seen that the only multiplication or division is, by virtue of the choice of coefficients, by an integer power of two, which readily may be accomplished within microcontroller 42 by shifting B(0), for example, right two bits.

At task block 308, a second Hanning filter is used to smooth the output of the IIR filter implemented at task block 306. This second Hanning filter processes the output of the first IIR filter by evaluating the expression $$D(0)=\tfrac{1}{4}[C(0)+2C(-1)+C(-2)] \qquad (6),$$

wherein C(p) are of course present and previous outputs of the IIR filter implemented at task block 306. Again, the multiplier by design is an integer power of two, rendering evaluation of the expression straightforward.

At task block 310, another first order, high-pass IIR filter is implemented, with the filter evaluating the expression $$F(0)=D(0)-E(0)/m \qquad (7),$$

where m=4 and where $$E(0)=D(-4)-D(0)-E(-1) \qquad (8),$$

wherein D(p) of course are present and previous outputs of the Hanning filter implemented at task block 308 and wherein E(−1) is the previous output of the present IIR filter implemented at task block 310. This IIR filter stage is designed also to roll off at 3-db/octave at, thereby substantially to block energy having a frequency less than, approximately 9-Hz.

At task block 312, a first order, low-pass IIR filter stage is encountered. Here, microprocessor 42 evaluates the expression $$G(0)=F(-4)-F(0)-G(-1) \qquad (9),$$

wherein of course F(p) are present and previous outputs of the high-pass IIR filter implemented at task block 310 and wherein G(−1) is the previous output of the present IIR filter implemented at task block 312. Preferably the gain of this low-pass IIR filter exhibiting 3-db/octave rolloff at approximately 14-Hz is four.

The result of digital signal processing in accordance with the invented method from the first and second Hanning filter digital smoothing stages, through the first and second high-pass IIR filter data processing stages and through the low-pass IIR filter digital processing stage is the production of modified ECG data from ADC 36 that is believed to be of greatest consequence in cardiac monitoring: data that represents electrical activity having a frequency between approximately 9-Hz and 14-Hz. Those of skill in the arts will appreciate that different fixed coefficients and variable digital sampling rates may be chosen to provide desirable frequency response characteristics that are different from those described and illustrated herein.

In accordance with the preferred method of the invention, the output of the illustrated ECG data digital filter is subject to further data processing at task block 314. Task block 314 preferably implements any suitable QRS complex detection and validation process, e.g. that described and illustrated in our U.S. Pat. No. 4,958,641, by which it is determined to a high degree of certainty when a QRS complex has occurred. Those of skill in the arts will appreciate that such task block 314 could instead be some other final or intermediate step in cardiac data monitoring, e.g. it might be determined instead whether a pulse from an implantable cardioverter/defibrillator monitor (ICDM) or pacer pulse instead is present in the patient's cardiography. Finally, at task block 316, control is RETURNed to other firmware routines executing concurrently in microprocessor 42 until such time as a new ECG datum is sampled by ADC 36. It will be appreciated that it is the sampling rate at which ADC 36 is programmed to operate that establishes the time base on which the digital filtering method of the invention operates.

The preferred method of the invention by which an ECG signal or successive ECG data samples digitally are filtered now may be understood by those skilled in the art. Preferably, the method involves first calculating a first filter output value that is equal to a first weighted average of plural ones of such successive samples, wherein the contributions of the ones of the samples to the weighted average are related to one another by powers of two. This first calculating step is realized in accordance with the preferred method by the execution of either or preferably both of task blocks 304, 308 by microcontroller 42. A second calculating step by which a second filter output value equal to a second weighted average of at least one of said previous output values from the first calculating step and at least one l5 output value of a previous one of the second calculating steps, wherein the contributions of said output values to the second weighted average are related to one another by powers of two is realized in accordance with the preferred method of the invention by execution of either or preferably both of task blocks 306, 310 by microcontroller 42. Preferably, these first and second calculating steps are performed by bit shifting, e.g. via execution of a bit shifting or rotating instruction in the microcontroller's arithmetic logic unit (ALU).

The third step of the preferred method involves repeating the first and second calculating steps to produce digitally filtered output data for further processing as a candidate QRS complex. This repeating step is implemented by microcontroller 42 repeatedly executing the routine illustrated in FIG. 6 by transferring control to START block 300.

Another way of describing the digital filtering method of the invention is that it involves sampling ECG data at a predetermined rate, e.g. a rate determined by microcontroller 42 at which ADC 36 is read; and calculating a filtered output value by evaluating an expression of the form of expression (2) above, e.g. microcontroller 42 executing task block 304, where X(0) is the current ECG data sample, X(−1) is the immediately preceding sample, X(−2) is the sample immediately preceding X(−1) and A(0) is the output value of the digital filter resulting from the evaluation, wherein m and n are integer powers of two, e.g. m=4 and n=2 as in expression (1) above.

Another way of describing the digital filtering method of the invention is this: sampling ECG data, calculating a filtered output value by evaluating an expression of the form of expression (2) above, e.g. microcontroller 42 executing task block 304, where X(0) is the current ECG data sample, X(−1) is the immediately preceding sample, X(−2) is the sample immediately preceding X(−1) and A(0) is the output value of the digital filter resulting from the evaluation, wherein m and n are integer powers of two, e.g. m=4 and n=2 as in expression (1) above and repeating the sampling and calculating steps, wherein said sampling of successive ECG data samples is performed at a rate (e.g. a rate determined by microcontroller 42 at which ADC 36 is read) calculated to provide a predetermined digital filter frequency response.

This way of describing the preferred digital filtering method of the invention points out a significant advantage of the invention: the firmware-imlemented and microcontroller-executed digital filter is dynamically programmable by very simply varying the frequency with which microcontroller 42 reads ADC 36, yet without any change to the power-of-two filter coefficients that have been determined empirically to provide optimal filtering of noise, motion and other potentially misleading artifacts from cardiac signals monitorable by apparatus 10. This facility equips wrist-worn cardiac monitor 10 with unprecedented versatility in and adaptability to the most demanding normal and abnormal cardiac and pacemaker or ICDM pulse monitoring applications.

Yet another way of describing the digital filtering method is as involving a first step of sampling an analog ECG signal at a predetermined frequency to produce a succession of plural signal-representative ECG data of a predetermined number p, e.g by rate-controllably reading ADC 36 by microcontroller 42 as illustrated in task block 302. The method involves then a second step of digitally filtering the ECG data produced by the sampling step by evaluating an expression of the form of expression (3) above, where X(p) is one of the succession of ECG data produced by the sampling step and where A(0) is the output value produced by the evaluation, wherein m is an integer power of two, e.g. preferably 4, wherein n is zero or an integer power of two, e.g. preferably 1, 2, 1 for the succession of samples and where p is an integer including zero, e.g. preferably 0,−1,−2 for the succession of samples. The expression evaluating part of this filtering step preferably is performed by bit shifting as described above.

The method next involves a third step of repeating the sampling and filtering steps to produce a succession of filtered output values produced by the evaluation and a fourth step of processing the succession into a record of filtered ECG data, e.g. microcontroller 42 repeatedly transfers control to START block 300 from which control is RETURNed at 316. It will be appreciated that Hanning filter-implementing task blocks 304, 308 shown in FIG. 6 are similar, but process different ECG data, and that, similarly, first order, high-pass IIR filter-implementing task blocks 306, 310 are similar, but process different ECG data. Preferably, a final step prior to QRS detection at 314 is low pass filtering at 312 in a manner very similar to, but with different ECG data and at higher gain than, the manner of the smoothing and high-pass filtering steps. Those of skill in the arts will appreciate that the filtering steps may be varied and/or reordered, within in the spirit of the invention, from that which is illustrated.

There is still another way of describing the digital filtering method of the invention: It may be seen to involve a first step of digitizing an analog ECG signal to produce a plurality of signal-representative ECG data bit strings with each datum including a plurality of bits at task block 302. A second step involves first shifting selected ones of the ECG data bits strings an integer number of bits in either direction in accordance with a first predetermined algorithm to produce a plurality of modified ECG data bit strings. A third step involves summing selected ones of the modified ECG data bit strings to produce a weighted average of the ECG data bit string plurality. A fourth step involves second shifting the weighted average an integer number of bits in either direction in accordance with a second predetermined algorithm to produce a filtered ECG data output bit string.

These second through fourth steps may be seen to be involved, for example, in the execution by microcontroller 42 of task block 304, wherein unshifted X(0), one bit left-shifted X(−1) (to effect multiplication by 2, which is an integer power of two) and unshifted X(−2) are summed to produce a weighted average which then is two bits right-shifted (to effect division by 4, which also is an integer power of two), thereby producing a single digital value A(0) that represents a smoothed, or averaged, version of the three successive measured ECG samples X(−2), X(−1), X(0). Those of skill in the arts will appreciate how straightforwardly such expression evaluation is performed by microcontroller 42 when the coefficients and multipliers are all integer powers of two. The preferred filtering methods described in different ways above may be seen straightforwardly to produce data that is relatively free of energy outside the normal range for a QRS complex, despite the relatively noisy input ECG signal environment in which dry skin electrodes are used.

It will be appreciated that the digital filtering methods described immediately above have been empirically determined reliably to discriminate digital data that is QRS complex candidate material from noise, motion and other artifacts. QRS detection may proceed at 314 by any known technique, but by the preferred method of the invention, is performed in accordance with the QRS validation teachings of U.S. Pat. No. 4,958,641. Thus the objects of the invention are achieved wherein an extremely compact, lightweight, wrist-worn monitor is equipped with the unprecedented capability of recording and playing back high-resolution, digital representations of a patient's cardiography for remote diagnosis or overread.

Accordingly, while a preferred embodiment of the invention has been described herein, and preferred methods associated therewith, it is appreciated that modifications are possible that are within the scope of the invention.

It is claimed and desired to secure by Letters Patent:

1. A wrist-worn monitor comprising:
 a housing suitable for attachment to a user's wrist;
 plural electrodes integral with said housing for contacting a patient's skin;
 signal detecting means integral with said housing and operatively connected with said electrodes for detecting cardiac activity represented by variations in the resistance of the patient's skin and for producing an ECG signal;
 an analog-to-digital signal converter integral with said housing and operatively connected with said signal detecting means and responsive to said ECG signal for producing ECG data;
 event detecting means integral with said housing and coupled with said converter for determining that a cardiac event has occurred, said event detecting means producing a trigger signal;
 recording means integral with said housing and coupled with said converter and said event detecting means and responsive to said trigger signal for recording selected EDG data proximate in time to such cardiac event; and
 transmitting means coupled with said recording means and integral with said housing for wirelessly communicating said recorder ECG data by producing a modulated ECG data carrier for telephonic transmission to a remote site.

2. The monitor of claim 1, wherein said electrodes are formed of a base metal a region of which is plated with a composition of titanium and at least one other element chosen from the group consisting of nitrogen and carbon.

3. The monitor of claim 2, wherein said composition is titanium nitride.

4. The monitor of claim 2, wherein said composition is titanium carbide.

5. The monitor of claim 2, wherein said composition is titanium carbo-nitride.

6. The monitor of claim 1 which further comprises implant detecting means integral with said housing and coupled with said converter and said recording means for detecting a pulse produced by an implanted pacemaker or defibrillator and for recording with an associated ECG data record an indicium of the occurrence of such pulse.

7. The monitor of claim 1 wherein said transmitting means includes a speaker for producing audible trans-telephonic communication of said recorded ECG data.

8. The monitor of claim 1 further comprising digital filtration means integral with said housing and coupled with said converter, said event detecting means and said recording means, wherein said digital filtration means performs the steps comprising:
 sampling said ECG data to produce a set of successive ECG data samples;
 a first calculating step whereby a first filter output value equal to a first weighted average of plural ones of said successive ECG data samples is calculated, wherein the contributions of said ones to said weighted average are related to one another by powers of two;
 a second calculating step whereby a second filter output value equal to a second weighted average of at least one previous of said first filter output values and at least one previous of said second filter output values is calculated, wherein the contributions of said output values to said second weighted average are related to one another by powers of two; and
 repeating said first and said second calculating steps to produce digitally filtered output ECG data for further processing by said event detecting means and said recording means as a candidate QRS complex.

9. The monitor of claim 1 further comprising:
 a battery integral with said housing and coupled with said converter, said event detecting means and said recording means; and
 battery end-of-life predicting means integral with said housing and coupled with said battery;
 wherein said battery end-of-life predicting means performs the steps comprising:
 predetermining a power capacity value for said battery; and repeatedly thereafter
  measuring the current drain on said battery while said monitor is being supplied with power therefrom,
  calculating the power being consumed by said monitor based upon said measuring, and
  comparing the result of said calculating with said power capacity value; then
 based upon said comparing, determining whether said consumed power is approximately equal to said power capacity value; and if so then
 annunciating on said monitor the impending end-of-life of said battery.

10. An ECG data monitor comprising:
 a unitary housing;
 plural electrodes integral with said housing for contacting a patient's skin;
 signal detecting means integral with said housing and operatively connected with said electrodes for detecting cardiac activity represented by variations in the resistance of the patient's skin and for producing an ECG signal;
 an analog-to-digital signal converter integral with said housing and operatively connected with said signal detecting means an responsive to said ECG signal for producing ECG data;
 recording means integral with said housing and coupled with said converter for recording ECG data; and
 transmitting means coupled with said recording means and integral with said housing for wirelessly communicating said recorded ECG data by producing a modulated ECG data carrier for telephonic transmission to a remote site.

* * * * *

UNITED STATES PATENT AND TRADEMARK OFFICE
CERTIFICATE OF CORRECTION

PATENT NO. : 5,289,824

DATED : March 1, 1994

INVENTOR(S) : Gary N. Mills and Habib Homayoun

It is certified that error appears in the above-identified patent and that said Letters Patent is hereby corrected as shown below:

Column 17, approximately line 42 change "EDG" to --ECG--.

Column 18, approximately line 58 before "responsive" change "an" to --and--.

Signed and Sealed this

Twenty-eighth Day of June, 1994

Attest:

BRUCE LEHMAN

*Attesting Officer*  *Commissioner of Patents and Trademarks*